(12) United States Patent  (10) Patent No.: US 7,429,270 B2
Baumgartner et al.  (45) Date of Patent: Sep. 30, 2008

(54) INTERVERTEBRAL IMPLANT (75) Inventors: Daniel Baumgartner, Oensingen (CH);
Martin Wymann, Liebefeld (CH);
Mario Gago Ho, Solothurn (CH);
Adrian Burri, Brig (CH)

(73) Assignee: Synthes (U.S.A.), West Chester, PA (US)

( * ) Notice: Subject to any disclaimer, the term of this patent is extended or adjusted under 35 U.S.C. 154(b) by 0 days.

(21) Appl. No.: 10/553,495

(22) PCT Filed: Apr. 14, 2003

(86) PCT No.: PCT/CH03/00247

§ 371 (c)(1),
(2), (4) Date: Jul. 25, 2006

(87) PCT Pub. No.: WO2004/089257

PCT Pub. Date: Oct. 21, 2004

(65) Prior Publication Data

US 2006/0265075 A1    Nov. 23, 2006

(51) Int. Cl.
*A61F 2/44* (2006.01)
(52) U.S. Cl. .............. 623/17.12; 623/17.11; 623/17.13; 623/17.14; 623/17.15; 623/17.16
(58) Field of Classification Search ... 623/17.11–17.16; 606/61, 246–279
See application file for complete search history.

(56) References Cited

U.S. PATENT DOCUMENTS

| | | | | |
|---|---|---|---|---|
| 3,867,728 | A * | 2/1975 | Stubstad et al. | 623/17.16 |
| 6,120,539 | A * | 9/2000 | Eldridge et al. | 623/11.11 |
| 6,419,704 | B1 | 7/2002 | Ferree | |
| 6,533,817 | B1 * | 3/2003 | Norton et al. | 623/17.16 |
| 6,626,943 | B2 * | 9/2003 | Eberlein et al. | 623/17.15 |
| 6,645,248 | B2 * | 11/2003 | Casutt | 623/17.12 |
| 6,733,533 | B1 * | 5/2004 | Lozier | 623/17.12 |
| 6,893,465 | B2 * | 5/2005 | Huang | 623/17.12 |
| 7,060,097 | B2 * | 6/2006 | Fraser et al. | 623/17.11 |
| 7,066,960 | B1 * | 6/2006 | Dickman | 623/17.16 |
| 2002/0123750 | A1 * | 9/2002 | Eisermann et al. | 606/69 |
| 2003/0045939 | A1 | 3/2003 | Casutt | |

(Continued)

FOREIGN PATENT DOCUMENTS

EP    0 346 129 A1    12/1989

(Continued)

*Primary Examiner*—Eduardo C. Robert
*Assistant Examiner*—Andrew Yang
(74) *Attorney, Agent, or Firm*—Stroock & Stroock & Lavan LLP (57) ABSTRACT

Disclosed is an intervertebral implant (1) comprising a central axis (2), a bottom cover plate (3) and a top cover plate (4), which are respectively provided with an exterior surface (7; 8) that extends transversal to the central axis (2), and a central part (10). Said central part (10) is located between the cover plates (3; 4) and is provided with a sleeve (12) encompassing a fiber system (5) that is connected to the cover plates (3; 4) and is embedded in an enveloping body (25) made of a homogeneous material. In analogy with the anatomic structure of the natural disk, the inventive intervertebral implant (1) can transfer occurring compressive forces onto the cover plates (3, 4) thereof as tensile forces that are applied to the individual fibers of the fiber system (5) thereof.

33 Claims, 4 Drawing Sheets

U.S. PATENT DOCUMENTS

| | | | |
|---|---|---|---|
| 2003/0135277 A1* | 7/2003 | Bryan et al. | 623/17.12 |
| 2003/0199984 A1* | 10/2003 | Trieu | 623/17.16 |
| 2004/0243238 A1* | 12/2004 | Arnin et al. | 623/17.12 |
| 2005/0197702 A1* | 9/2005 | Coppes et al. | 623/17.12 |

FOREIGN PATENT DOCUMENTS

| | | |
|---|---|---|
| WO | WO 93/16664 | 9/1993 |
| WO | WO 02/17825 | 3/2002 |

* cited by examiner

INTERVERTEBRAL IMPLANT

The invention concerns an intervertebral implant according to the preamble of patent claim 1.

An intervertebral disc prosthesis of the generic type is known from U.S. Pat. No. 4,911,718 Lee. This known intervertebral disc prosthesis comprises a central core, that is so formed from a biocompatible elastomer, that it is almost corresponds to that of the nucleus pulposus of a natural intervertebral disc, as well as from a multi-layer laminate from fibres bound in an elastomer, arranged around the core. Each laminate layer has its own yarn system, so that a plurality of fibre groups are present. The fibres of the individual layers have various orientations, whereby the angles of the fibres relative to the central axis of the intervertebral disc are in the range of ±20° and ±50°, preferably 0°, +45° and −45°.

From WO 90/00374 Klaue a hip prosthesis is known, the shaft of which is made from a tubular mesh, i.e. a structure, that comprises at least two series of fibres crossing one another. In this application the interior of the tubular mesh remains empty as the shaft of the femur component.

In the case of the prosthesis disclosed in U.S. Pat. No. 4,911,718 Lee, although the individual fibres are integrated in the laminate that is made from an elastomer or another type of synthetic material, their ends are, however, adhered only to the end plates, so that they do not surround the core and consequently, in the case of a radial expansion of the core, cannot accept any tensile force. When adhering the lateral walls, cut out from the fibrous matrix compound, to the end plate, a fixing of the integrated fibres on the end plate is quite difficult, only the cross-section of the fibre offers a contact surface for the chemical joint. Therefore increased stresses occur especially on these joining places of the fibres on the end plate.

Furthermore, in the case of Lee the length of the individual fibres is only from the bottom cover plate to the top cover plate, what corresponds to the sheathing height or a diagonal of the projected sheathing height. Thus the forces occurring can be reduced only along these lengths due to the transfer of the shearing force of the fibres to the elastomer. Thus positions of increased stresses result at the fixings, i.e. on the ends of the fibres.

The prosthesis disclosed in WO 90/00374 Klaue comprises a system of fibres, the individual fibres of which are not fixed on both ends, as well as there is no deformable core. Therefore in the case of an axial compression of the prosthesis the axial compression forces occurring cannot be transferred as tensile forces to the fibres.

From U.S. Pat. No. 3,867,728 Stubstad et al. an intervertebral disc prosthesis is known, that has an elastomeric sandwich structure with a fibre system. A disadvantage of this known prosthesis is that the fibre system, joined with the cover plates, is either not embedded in the sheathing body or in another embodiment is embedded in a multi-layer laminate of an elastomer.

This is where the invention wants to provide remedy. The object of the invention is to produce an intervertebral implant, that comprises a fibre system joined with the cover plates, by virtue of which a sheathing body, surrounding the central part and made from a homogeneous material, will be reinforced.

The inventions achieves this objective with an intervertebral implant having the features of claim 1.

The basic advantages, achieved by the invention, are that with the intervertebral implant according to the invention
- the fibre system can be first wound around the central part and following this poured into an elastomer forming the elastic sheathing body, so that the sheathing, enveloping the central part, can be easily produced,
- by applying the elastic material around the fibre system after its winding, the anchoring of the fibre system is possible by various means, for example also on the opposing inner surfaces of the cover plates,
- the central part allows a movement of both adjacent bodies of the vertebra in the case of a compression, flexion or extension, lateral bending and torsion,
- the momentary centre of rotation or the momentary axes of rotation are not determined by the intervertebral implant itself, and they can position themselves according to the rule of minimum forces or moments occurring,
- by varying the number of fibres in the circumferential direction, the cross-section of the fibres and the choice of material, the behaviour of the intervertebral implant can be so adjusted, that under varying loads the movements occur as in the case of the natural intervertebral disc, and
- by varying the arrangement and the execution of the fibre system certain movement limitations can be placed on the intervertebral implant, and from a certain deformation a limit region occurs, where despite the further increasing forces no deformation takes place or in the case of moments occurring the implant will no longer tilt.

The axial compression forces occurring under a load on the spinal column are transmitted to the central part via the two end plates. The compression forces deform the central part situated between the two end plates, in particular an elastic formed body situated therein, in such a manner that the central part radially buckles. This expansion of the central part is restricted by the fibre system surrounding the central part and the radial compression forces arising can be absorbed by the fibre system as a tensile force. Thus a further, disadvantageous buckling of the central part can be limited. By anchoring the fibre system in both cover plates, the intervertebral implant remains stable even under the greatest loads and the fibre system is capable to withstand even considerable tensile forces.

In a preferred embodiment the entire fibre system is embedded in the elastic sheathing body, so that the fibre system does not necessarily need to be made from a biocompatible material.

In a further embodiment the fibre system is only partially embedded in the elastic sheathing body, while the fibre system has a radial thickness $\delta$ relative to the central axis and the elastic sheathing body has a radial thickness d, and the $\delta/d \times 100\%$ ratio is in a range of 80% and 350%. By virtue of this the advantages can be achieved, that the large relative movements in the peripheral region of the cover plates occurring during a flexion/extension movement-or a lateral movement of the adjacent bodies of the vertebra are not subjected to a great resistance by the elastic sheathing body and due to this the danger of a fissure formation in the sheathing body is slighter.

The embedding of the fibre system in the elastic sheathing body can be carried out various embodiments in such a manner, that
 a) the fibre system can be moved relative to the elastic material of the sheathing body, or
 b) the fibre system cannot be moved relative to the elastic material of the sheathing body.

In yet another embodiment the entire fibre system is anchored on the cover plates, so that greater tensile forces can be accepted by the fibre system, and consequently the intervertebral implant obtains a great torsional rigidity.

In another embodiment the sheathing body, accommodating the fibre system, is made from an elastic, biocompatible material, preferably an elastomer, produced in particular based on polyurethane (PUR). However, silicone rubber, polyethylene, polycarbonate urethane (PCU) or polyethylene terephthalate (PET) may also be used.

In yet another embodiment the central part is filled at least partially with an incompressible medium, preferably a liquid.

In another embodiment the central part comprises an incompressible liquid core and an elastic formed body provided around it, while the liquid can be accommodated, for example, in a cavity provided in the formed body. This brings with it the advantage, that by virtue of the liquid core a mechanical behaviour of the intervertebral implant is similar to that of a physiological intervertebral disc. The axial deformation of the elastic central part will result in the radial expansion of the incompressible liquid and consequently in the radial expansion of the wall of the central part containing the fibre system. The tensile forces, occurring due to the radial expansion and/or the buckling of the wall of the central part, are basically absorbed by the fibres.

The anchoring of the fibres on the cover plates can be carried out, for example, in the following manner:

a) Mechanically by guiding the endless fibres through grooves and over the external surfaces of the cover plates from one groove to another one. Thus the fibres surround the central part together with the cover plates. By guiding the fibres in the grooves the fibre system can be so anchored on the cover plates, that in the case of tensile forces acting on the fibres no slipping of the fibres on the lateral sides is possible because the fibres can absorb only tensile forces, b) Mechanically by a wedge-shaped construction of the grooves, so that the fibres extending from cover plate to cover plate can be firmly clamped in the grooves, and/or c) By adhering the fibre system on the cover plates.

In yet another embodiment of the intervertebral implant according to the invention each cover plate comprises on its periphery a lateral surface and grooves distributed on the circumference and radially penetrating into the lateral surfaces. The fibres, part of this fibre system, are guided through these grooves.

In a further embodiment the central part and the fibre system are joined with the cover plates in a form-locking manner.

In yet a further embodiment the fibre system is guided over the external surfaces of both cover plates, so that it will surround the central part as well as the cover plates.

When using an endless fibre, that covers the entire implant, the stresses preferably are distributed on the entire circumference of this winding. The fibre system is preferably in the form of a woven material, fabric or is knitted.

In another embodiment channels are mortised in the external surfaces of the cover plates to accommodate the fibre system.

In yet another embodiment the central part is essentially hollow-cylindrical, hollow-prismatic or is a body of rotation, an ellipsoid, a partial sphere or barrel-shaped with an axis of rotation that is coaxial with the central axis. By virtue of such configurations the advantage, that the positions of the axes of rotation of the adjacent intervertebral discs correspond, as far as possible, to that of the natural intervertebral disc, can be achieved.

The fibre system can be made, for example, from UHMWPE (ultra high molecular weight polyethylene) or from PET (polyethylene terephthalate).

In a further embodiment of the intervertebral implant according to the invention a closing plate is fastened on each cover plate for placing the adjacent bodies of the vertebra on the base plate or cover plate, each of the said closing plate having an external surface at right angles to the central axis with a macroscopic structure. The structure may be, for example, in the form of teeth. The macroscopic structure allows a primary stabilisation of the intervertebral implant immediately after the operation. Thus a mechanical anchoring of the intervertebral implant at a time when the growing of the bone on the intervertebral implant has not yet taken place, can be achieved.

In yet a further embodiment the woven material is formed from first and second fibres, wherein the first fibres include an angle $\alpha$ with the central axis and the second fibres include an angle $\beta$ with the central axis. The angles for $\alpha$ or $\beta$ are preferably between 15° and 60°.

In another embodiment the first and second fibres are interwoven with one another.

In yet another embodiment the elastic formed body has at right angles to the central axis a cross-sectional surface $F_F$, while the central part has at right angles to the central axis a cross-sectional surface $F_M$ and the $F_F/F_M$ ratio of these two cross-sectional surfaces is between 30% and 65%.

In a further embodiment the elastic formed body is surrounded by a semi-permeable membrane, while in the interior of the elastic formed body preferably physiological table salt solution is present.

With regard to the central axis the fibre system may be single-layered or multi-layered, preferably 2-6 layered. Furthermore, the fibre system can be wound on the elastic formed body. The winding on the elastic formed body can be in two different directions, preferably rotationally symmetrically.

In yet another further embodiment a closing plate can be fastened on each cover plate, the closing plate having at right angles to the central axis an external surface with a macroscopic structure, preferably in the form of teeth.

The diameter of the fibres is in a range of 0.005 mm and 0.025 mm. A yarn (roving) is preferably produced from a plurality of fibres, whereby 500-2000 fibres form a yarn with a cross-sectional surface of 0.5 mm² to 2 mm².

In those embodiments, wherein the fibre system has fibre sections crossing one another, in the case of flexion movements (flexion, extension, lateral flexion) of the patients some fibre sections will be unilaterally clamped and in case of shearing the fibre sections extending tangentially to the shearing direction absorb the forces.

The invention and developments of the invention are explained in detail in the following based on partially schematic illustrations of several embodiments. They show in.

Figure 1:
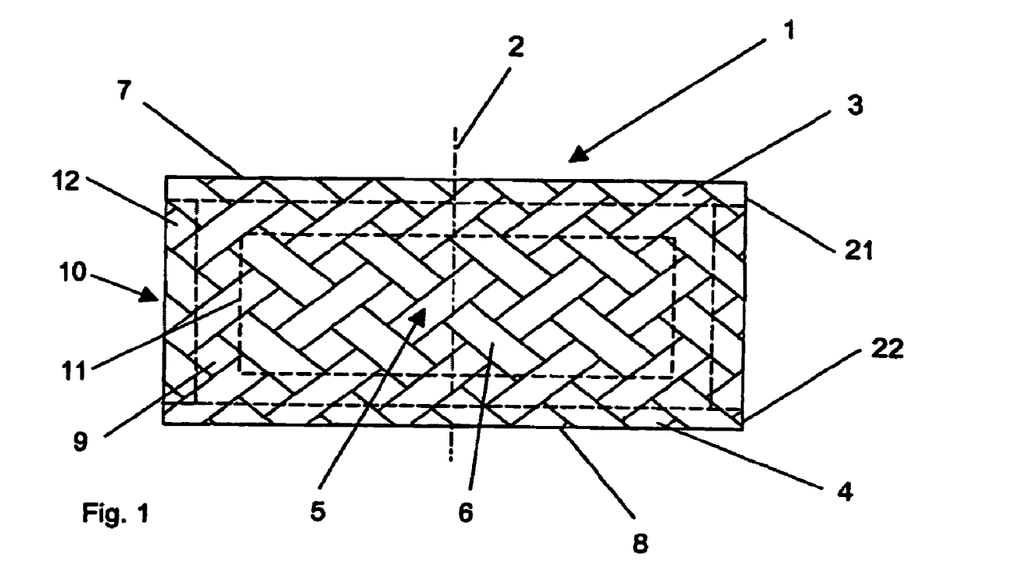
FIG. 1—a side view of an embodiment of the intervertebral implant according to the invention, FIG. 2—a top view on the embodiment of the intervertebral implant according to the invention, illustrated in FIG. 1, FIG. 3—a side view of another embodiment of the intervertebral implant according to the invention, FIG. 4—a section through the embodiment of the intervertebral implant according to the invention, illustrated in FIG. 3, FIG. 5a—a perspective illustration of the fibre system of an embodiment of the intervertebral implant according to the invention, FIG. 5b—a top view on the fibre system illustrated in FIG. 5a, FIG. 6a—a perspective illustration of the fibre system of an embodiment of the intervertebral implant according to the invention, FIG. 6b—a top view on the fibre system illustrated in FIG. 6a, and FIG. 7—a section through a further embodiment of the intervertebral implant according to the invention.
Figure 2:
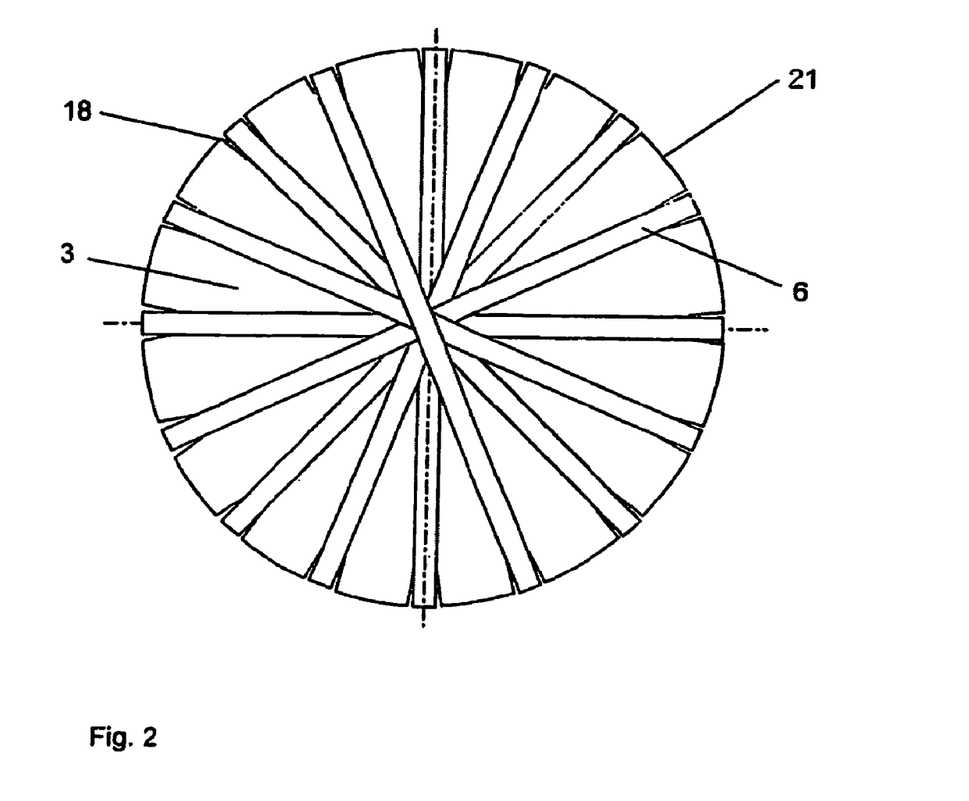

FIGS. 1 and 2 illustrate an embodiment of the intervertebral implant 1 according to the invention, that comprises a top cover plate 3 and a bottom cover plate 4, each with an external surface 7, 8 extending at right angles to the central axis 2 and having a lateral surface 21, 22 on the periphery. Between the cover plates 3, 4 there is a central part 10 provided with a central cavity 11 and a sheathing 12, that surrounds the fibre system 5. For the purpose of anchoring the fibres 6 of the fibre system 5 on the cover plates 3, 4, each of the peripheral lateral surfaces 21, 22 has grooves 18, distributed on the circumference and radially protruding into the lateral surfaces 21, 22, so that the fibre system 5 can be anchored in these grooves 18. In the central cavity 11 there is an elastically deformable formed body 9 with an incompressible core, preferably a liquid core 13. Due to the incompressibility of the liquid core 13 during a compression of the cover plates 3, 4 parallel to the longitudinal axis 2, for example, the elastic formed body 9 and the sheathing 12 with the fibre system 5 will buckle radially, i.e. at right angles to the longitudinal axis 2, consequently the fibres 6 will be under tension.

Figure 3:
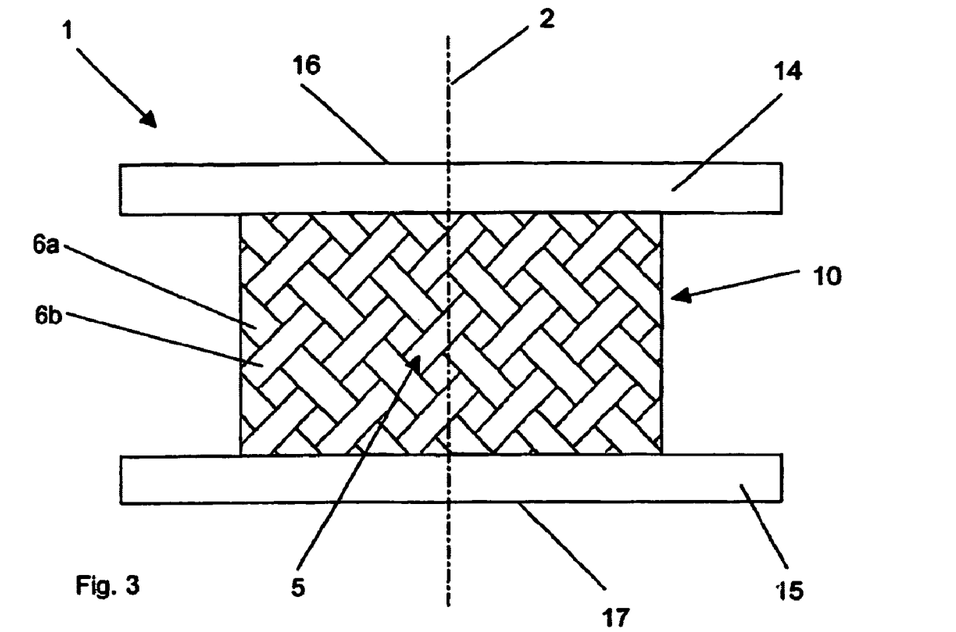
Figure 4:
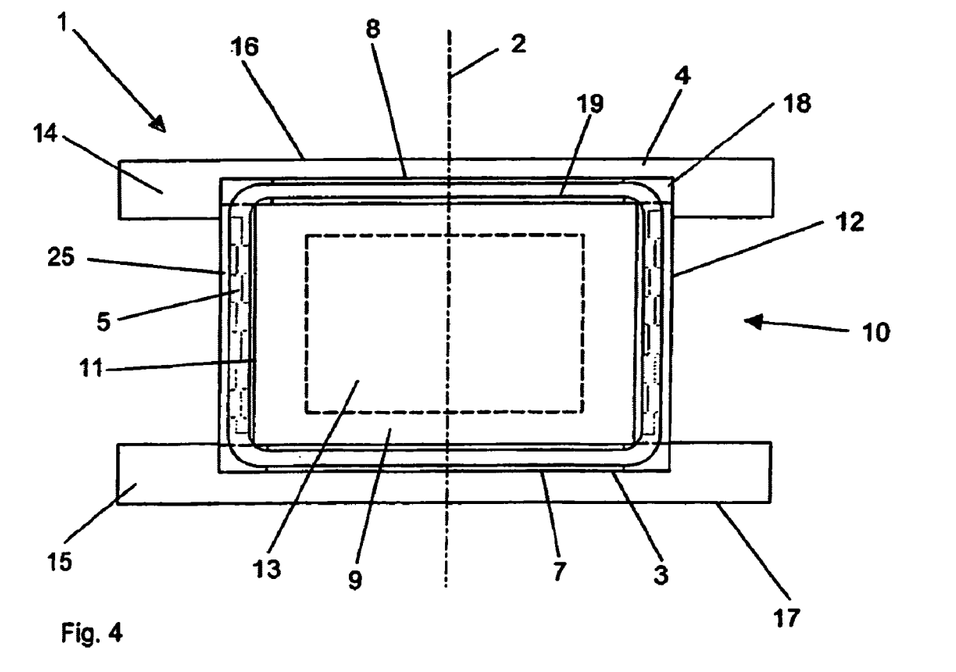

FIGS. 3 and 4 illustrate an embodiment of the intervertebral implant 1 according to the invention, that comprises two cover plates 3, 4, provided at right angles to the central axis 2, and an elastically deformable central part 10 situated between them. The central part 10 comprises a hollow-cylindrical sheathing 12 that is coaxial with the central axis 2 and a central cavity 11. In the central cavity 11 an elastic formed body 9 with an incompressible core is provided, preferably a liquid core 13. The formed body 9 is surrounded by a semi-permeable membrane, whereas the sheathing 12, that surrounds the fibre system 5 and an elastic sheathing body 25 passed through by the fibre system 5, is made from a synthetic material. The closing plates 14, 15 are firmly joined with the cover plates 3, 4 and have axially protruding surfaces 16, 17, which can be brought to rest on the end plates of two adjacent bodies of the vertebra. The fibre system 5 is anchored on the cover plates 3, 4 and is integrated in the sheathing 12 and its purpose is to absorb the forces on the central part 10, said forces acting on the intervertebral implant 1 via the bodies of the vertebra adjacent to the closing plates 14, 15, i.e. torsional forces due to the rotation of the bodies of the vertebra about the central axis 2 relative to one another or bending moments due to lateral bending and/or flexion/extension of the spinal column. For example, a compression force, acting on the intervertebral implant 1 parallel to the central axis 2, is transferred by both closing plates 14, 15 via both cover plates 3,4 to the central part 10, while as the result the elastic formed body 9 will buckle at right angles to the central axis 2. This expansion movement of the elastic formed body 9 is transferred to the sheathing 12 with the fibre system 5 and contained by this. Since the fibre system 5 is anchored on the cover plates 3, 4, the compression force, acting transversely to the central axis 2, generates tensile forces in the fibres of the fibre system 5. The fibre system 5 in this case is made from synthetic fibres, preferably from UHMWPE-fibres (ultra high molecular weight polyethylene) or from PET (polyethylene terephthalate) and comprises a mesh from first and second fibres 6a, 6b, that are interwoven with one another. By doing so, the first fibres 6a include an angle α and the second fibres 6b an angle β with the central axis 2. In the embodiment of the intervertebral implant 1 according to the invention illustrated here, the angles α and β are equal and are between 15° and 60°. The fibres 6a, 6b are anchored on the cover plates 3, 4 by means of grooves 18 that are arranged on the circumference of the cover plates 3, 4 parallel to the central axis 2, so that the fibres 6a, 6b are passed through the grooves 18 and can be guided to the next groove 18 over the surfaces 7, 8 in a channel 19. The cover plates 3, 4 are made from synthetic material, whereas the closing plates 14, 15, arranged externally, are made from titanium or a titanium alloy. The externally arranged closing plates 14, 15 are joined with the cover plates 3, 4 either by form-locking or frictional locking. In particular they can be adhered or welded to one another.

Figure 5A:
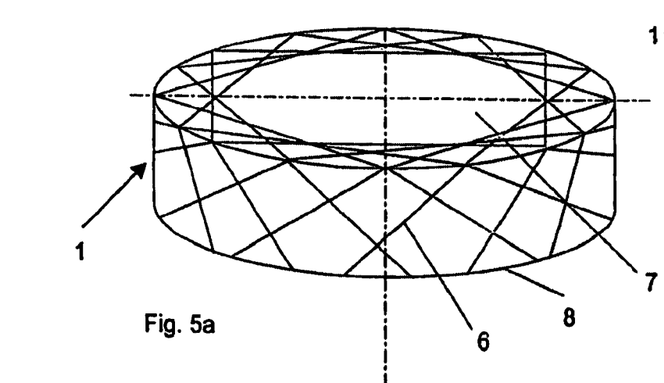
Figure 5B:
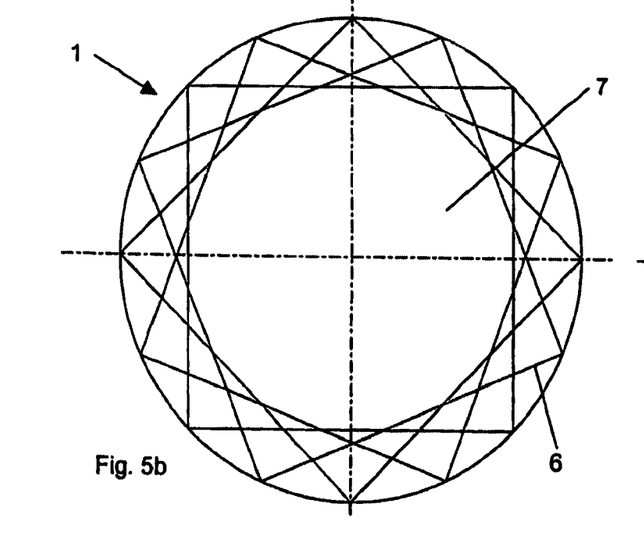

In FIGS. 5a and 5b a fibre system 5 is illustrated according to an embodiment of the intervertebral implant 1 according to the invention, wherein the fibres 6 extending over the end plates 3, 4 form chords on the circular surfaces 7, 8 of the cover plates 3, 4.

Figure 6A:
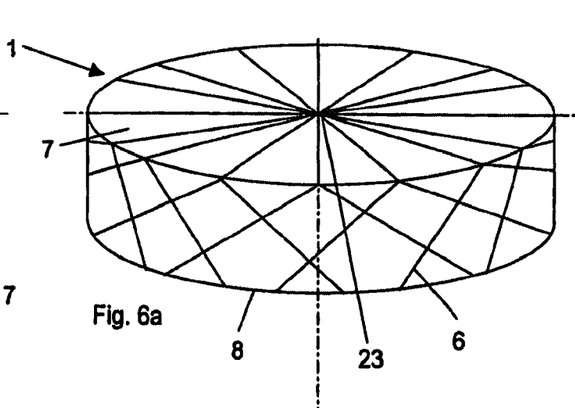
Figure 6B:
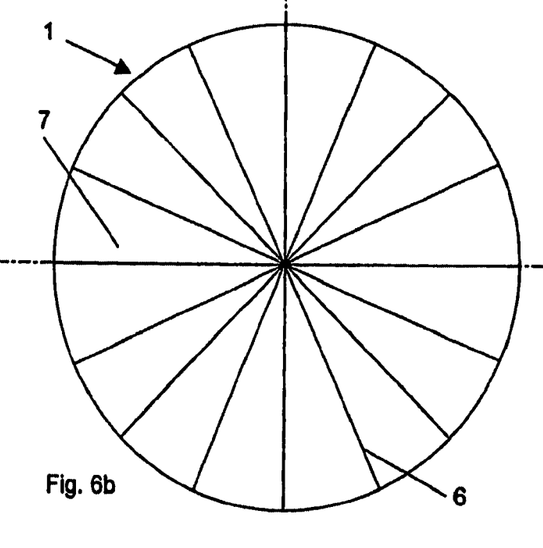

In FIGS. 6a and 6b a fibre system 5 is illustrated according to an embodiment of the intervertebral implant 1 according to the invention, wherein the fibres 6 extending over the end plates 3, 4 cross at the point of intersection of the central axis 2 and the end plates 3, 4.

When compared with the arrangement of the fibres 6 (FIGS. 6a, 6b), the guiding of the fibres 6 as chords (FIGS. 5a, 5b) over the surfaces 7, 8 of the end plates 3, 4 has the following advantages:

- due to the better distribution of the crossing points of the fibres 6 no concentration will occur, especially between the external surfaces 7, 8 of the cover plates 3, 4 and the closing plates 14, 15 (FIGS. 3 and 4), and
- with the aid of a winding technique the fibre system 5 can be symmetrically produced relative the central axis 2 while the intervertebral implant 1 can be clamped in at the points of intersection between the central axis 2 and the cover plates 3, 4.

Figure 7:
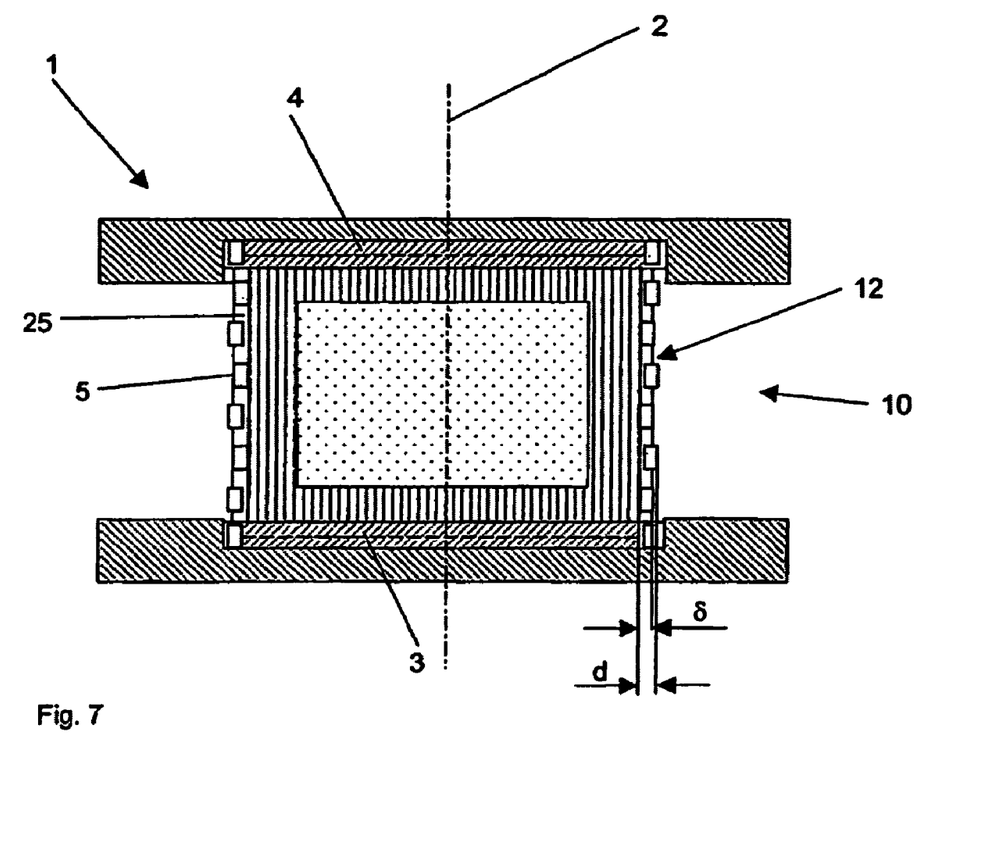

FIG. 7 illustrates an embodiment, that differs from the embodiment illustrated in FIGS. 3 and 4 only by that the periphery of the sheathing 12 provided on the central part 10 comprises an elastic sheathing body 25 only partially passed through by the fibre system 5, the thickness of the sheathing body d being smaller than the radial thickness δ of the fibre system.

The invention claimed is:

1. An intervertebral implant for implantation between adjacent vertebrae, the implant having a central axis, the implant comprising:
    a bottom closing plate having an external surface extending generally transversely to the central axis for contacting at least a portion of one of the adjacent vertebrae;
    a bottom cover plate in contact with the bottom closing plate, wherein at least one of the bottom closing plate and the bottom cover plate is substantially rigid;
    a top closing plate having an external surface extending generally transversely to the central axis for contacting at least a portion of the other adjacent vertebrae;
    a top cover plate in contact with the top closing plate, wherein at least one of the top closing plate and the top cover plate is substantially rigid;
    a central part provided between the top and bottom closing plates, the central part including a fiber system and a core, the fiber system being at least partially joined to the cover plates, and at least partially surrounding the core, and
    a sheathing comprising an elastic sheathing body, the sheathing body at least partially surrounding the central part and being connected to the top and bottom cover plates;
    wherein the core is an elastically formed body having a cavity, the cavity being filled at least partially with an incompressible liquid, the liquid being at least partially surround by the elastic formed body, the fiber system being wound on the elastic formed body.

2. The intervertebral implant according to claim 1, wherein the fiber system is embedded in the elastic sheathing body.

3. The intervertebral implant according to claim 1, wherein the fiber system has a radial thickness δ relative to the central axis and the sheathing body has a radial thickness d, wherein δ divided by d times 100 % is in a range between 80 % and 350 %.

4. The intervertebral implant according to claim 1, wherein the fiber system can move relative to the sheathing body.

5. The intervertebral implant according to claim 1, wherein the fiber system is mounted so that said fiber system cannot move relative to the sheathing body.

6. The intervertebral implant according to claim 1, wherein the entire fiber system is joined with the top and bottom cover plates.

7. The intervertebral implant according to claim 1, wherein the sheathing body is made from an elastomer selected from the group consisting of polyurethane, silicone rubber, polyethylene, polycarbonate urethane and polyethylene terephthalate.

8. The intervertebral implant according to claim 1, wherein the fiber system is mechanically anchored on or in the cover plates.

9. The intervertebral implant according to claim 1, wherein the fiber system is adhered to the cover plates.

10. The intervertebral implant according to claim 1, wherein the fiber system is joined with the cover plates in a form-locking manner.

11. The intervertebral implant according to claim 1, wherein the fiber system is formed by an endless fiber.

12. The intervertebral implant according to claim 1, wherein the top and bottom cover plates include a plurality of grooves for anchoring the fiber system.

13. The intervertebral implant according to claim 1, further comprising a plurality of channels mortised in an external surfaces of the cover plates to accommodate the fiber system.

14. The intervertebral implant according to claim 1, wherein the fiber system is formed by a woven material.

15. The intervertebral implant according to claim 14, wherein the woven material is formed from first and second fibers and the first fibers include an angle α with the central axis and the second fibers include an angle β with the central axis.

16. The intervertebral implant according to claim 15, wherein the first and second fibers are interwoven with one another.

17. The intervertebral implant according to claim 15 wherein the angle α is between 15 degrees and 60 degrees.

18. The intervertebral implant according to claim 15 wherein the angle β is between 15 degrees and 60 degrees.

19. The intervertebral implant according to claim 1, wherein the core is selected from the group consisting of a hollow-cylindrical, a hollow-prismatic an ellipsoid, a partial sphere or a barrel-shaped with an axis of rotation that is coaxial with the central axis.

20. The intervertebral implant according to claim 1, wherein with regard to the central axis the fiber system is single-layered.

21. The intervertebral implant according to claim 1, wherein with regard to the central axis the fiber system is multi-layered.

22. The intervertebral implant according to claim 1, wherein the fiber system is wound on the elastic formed body in two different directions.

23. The intervertebral implant according to claim 1, wherein the fiber system is made from UHMWPE (ultra high molecular weight polyethylene).

24. The intervertebral implant according to claim 1, wherein at least one of the closing plates includes at least one external surface feature on the external surface for anchoring the implant to one of the adjacent vertebrae.

25. The intervertebral implant according to claim 1, wherein the fibers have a diameter, the diameter being in the range of 0.005 mm and 0.025 mm.

26. The intervertebral implant of claim 1, wherein the top and bottom closing plates are made from titanium or a titanium alloy.

27. The intervertebral implant of claim 1, wherein the bottom cover plate and the top cover plate are joined to the bottom closing plate and the top closing plate, respectively.

28. The intervertebral implant of claim 1, wherein the bottom and top closing plates are substantially rigid.

29. An intervertebral implant for implantation between an upper and lower vertebrae, the implant having a central axis, the implant comprising:
   a first substantially rigid bone contacting plate having an external surface extending generally transversely to the central axis for contacting at least a portion of the upper vertebra;
   a second substantially rigid bone contacting plate having an external surface extending generally transversely to the central axis for contacting at least a portion of the lower vertebra;
   a third plate operatively coupled to the first bone contacting plate, the third plate including a plurality of openings;
   a fourth plate operatively coupled to the second bone contacting plate, the fourth plate including a plurality of openings;
   a central part substantially located between the third and fourth plates, the central part including a flexible core and a fiber system, wherein the core is substantially cylindrical and includes a top surface and a bottom surface, the top surface of the core being in contact with the third plate and the bottom surface of the core being in contact with the fourth plate, and wherein the fiber system at least partially surrounds the core, and is at least partially received within the plurality of openings formed in the third and fourth plates so that the fiber system is joined to the third and fourth plates; and
   an elastic sheathing body at least partially surrounding the fiber system and the core, and connected to the third and fourth plates.

30. The intervertebral implant of claim 29, wherein the first and second bone contacting plates are made from titanium or a titanium alloy 31. The intervertebral implant of claim 30, wherein the fiber system is constructed of an ultra high molecular weight polyethylene (UHMWPE) material.

32. The intervertebral implant of claim 29, wherein the elastic sheathing body contacts at least a portion of a top surface of the third plate and at least a portion of a bottom surface of the fourth plate.

33. An intervertebral implant for implantation between adjacent vertebrae, the implant having a central axis, the implant comprising:
   a bottom closing plate having an external surface extending generally transversely to the central axis for contacting at least a portion of one of the adjacent vertebrae;
   a bottom cover plate in contact with the bottom closing plate, wherein at least one of the bottom closing plate and the bottom cover plate is substantially rigid;

a top closing plate having an external surface extending generally transversely to the central axis for contacting at least a portion of the other adjacent vertebrae;

a top cover plate in contact with the top closing plate, wherein at least one of the top closing plate and the top cover plate is substantially rigid;

a central part provided between the top and bottom closing plates, the central part including a fiber system and a core, the fiber system being at least partially joined to the cover plates, and at least partially surrounding the core, and a sheathing comprising an elastic sheathing body, the sheathing body at least partially surrounding the central part and being connected to the top and bottom cover plates;

wherein the core is an elastically formed body having a cavity, the cavity being filled at least partially with an incompressible liquid, the liquid being at least partially surround by the elastic formed body; and wherein the elastic formed body is surrounded by a semi-permeable membrane.

* * * * *

UNITED STATES PATENT AND TRADEMARK OFFICE
CERTIFICATE OF CORRECTION

PATENT NO. : 7,429,270 B2 Page 1 of 1
APPLICATION NO. : 10/553495
DATED : September 30, 2008
INVENTOR(S) : Daniel Baumgartner et al.

It is certified that error appears in the above-identified patent and that said Letters Patent is hereby corrected as shown below:

Column 7, line 1 reads -- surround by the elastic formed body, the fiber system -- should read -- surrounded by the elastic formed body, the fiber system --.

Column 7, line 39 reads -- surfaces of the cover plates to accommodate the fiber system -- should read -- surface of the cover plates to accommodate the fiber system --.

Column 7, line 56 reads -- hollow-cylindrical, a hollow-prismatic an ellipsoid, a partial -- should read -- hollow-cylindrical, a hollow-prismatic, an ellipsoid, a partial --.

Column 10, line 8 reads -- surround by the elastic formed body; and -- should read -- surrounded by the elastic formed body; and --.

Signed and Sealed this

Twenty-sixth Day of May, 2009

JOHN DOLL
*Acting Director of the United States Patent and Trademark Office*